United States Patent [19]

Parks

[11] Patent Number: 5,050,600
[45] Date of Patent: Sep. 24, 1991

[54] CARDIAC PACEMAKER

[76] Inventor: Lance K. Parks, 311 Parkhill, Billings, Mont. 59101

[21] Appl. No.: 415,600

[22] Filed: Oct. 2, 1989

[51] Int. Cl.⁵ ............................................. A61N 1/00
[52] U.S. Cl. .................................. 128/419 P; 128/785
[58] Field of Search ............. 128/419 P, 419 PG, 783, 128/784, 785

[56] References Cited

U.S. PATENT DOCUMENTS

| | | | |
|---|---|---|---|
| 3,807,411 | 4/1974 | Harris et al. | 128/419 P |
| 3,945,387 | 3/1976 | Adams | 128/419 PG |
| 4,136,702 | 1/1979 | Trabucco | 128/419 P |
| 4,177,818 | 12/1979 | De Pedro | 128/785 |
| 4,858,623 | 8/1989 | Bradshaw et al. | 128/785 |

Primary Examiner—Francis Jaworski
Assistant Examiner—George Manuel
Attorney, Agent, or Firm—Richard C. Conover

[57] ABSTRACT

A battery-powered pacemaker includes an electrical pulse generating device enclosed in a portable case. The pulse generating device is connected to a disposable electrode insertion unit that can easily be inserted in a patient's heart. A relatively short conductive lead connects the pulse generating device and the electrode insertion unit. The case of this pacemaker can be placed on the patient or near the side of the patient but out of the way, thus eliminating the use of the long conductive leads which has been a problem in the past. The present pacemaker also used a male connector on the case to receive a female connector attached to the conductive lead. The male/female connector is used so that blood and other contaminants can be easily cleaned from the male fitting before the unit is reused. Barbless hooks attached to one side of the electrrode insertion unit are used for electrically connecting the pulse generating means device to the heart.

3 Claims, 1 Drawing Sheet

CARDIAC PACEMAKER

BACKGROUND OF THE INVENTION

This invention relates to a temporary and disposable ventricular cardiac pacemaker, and more particularly to a pacemaker which transmits pulses at a selected rate to barbless hook electrodes that are inserted and held in a patient's heart.

In cardiopulmonary bypass surgery, the heart is generally stopped during surgery, and an oxygenator is used to supply blood to the patient during the surgical operation. Upon completion of surgery, it is frequently necessary to restart the heart by stimulating the heart muscle with an electrical pulse. To do this, surgeons use a temporary pacemaker device.

Further, during circumstances when the heart stops or is too slow to function properly prior to cardiopulmonary bypass, there is need for a temporary device which can be applied quickly and removed easily once cardiopulmonary bypass has been initiated.

The temporary pacemaker devices in use today have two separate wires, each approximately two feet long with each wire having a sterile needle attached at an end thereof. With these devices, the wires are surgically stitched to the heart tissue to provide an electrical connection. After connecting the wires to the heart, the needles are then pushed through the chest wall, at a position spaced from the incision used for heart surgery, and the wires are led outside the chest wall. The needles are formed so that each may be snapped in two leaving a stub still connected to the corresponding wire. The stub is then inserted in a female electrical connector connected to an electrical cable which in turn is connected to an external, battery-operated, pulse generator which is used to provide electrical pulses to the heart.

With these conventional temporary pacemakers wires are connected to the pulse generator and are subject to being knocked loose and must be repositioned or replaced. Upon completion of surgery, the pacemaker wires must either be removed or passed through the skin of the chest wall.

There is a recognized need for a temporary pacemaker assembly which can be used briefly during surgery until the heart starts beating on its own, to provide an effective means for attaching electrodes to the heart while avoiding the use of stitched connections and long leads that can be knocked loose. There is also a need for a pacemaker where any leads or electrodes used with a particular patient can be disposed of after use at the conclusion of surgery. Further, there is a need for a temporary pacemaker where the connector between the pacemaker pulse transmitting portion and the pacemaker lead can readily be cleaned of blood or other contaminants before the pulse transmitting portion of the assembly is reused.

Pacemaker devices are well known and the electrode assemblies for attaching pacemaker electrodes to a patient's heart are also known in the art. U.S. Pat. No. 4,607,644 to Pohndorf and U.S. Pat. No. 4,177,818 to De Pedro both illustrate barbless hook electrodes which can be inserted into a heart, the electrodes receiving electrical pulses to stimulate a patient's heart. In both of these patented devices, the electrodes are intended to be used with pacemakers implanted under a patient's skin and thus are designed for long-term implantation. The electrodes are not easily used in a surgical environment for temporary use.

SUMMARY OF INVENTION

The present invention relates to a battery-powered electrical pulse generating device enclosed in a portable case. The pulse generating device is connected to a disposable electrode insertion unit that can easily be inserted in a patient's heart. A relatively short conductive lead connects the pulse generating device and the electrode insertion unit. The pacemaker case can be placed on the patient or near the side of the patient but out of the way, thus eliminating the use of long conductive leads which has been a problem in the past. The present pacemaker also uses a male connector on the case to receive a female connector attached to the conductive lead. The male/female connector is used so that blood and other contaminants can be easily cleaned from the male fitting before the unit is reused. Barbless hooks attached to one side of the electrode insertion unit are used for electrically connecting the pulse generating means device to the heart.

The electrode insertion unit is formed with first and second planar members hingedly connected together. The barbless-hook electrodes extend in parallel arcs from the underside of the second planar member. On the top surface of the second planar member, an easily-grasped gripping tab protrudes upwardly to enable a surgeon to manipulate the barbless hooks during insertion of the hooks in the heart. As the barbless hooks are pushed with sufficient force to pierce the heart muscle, the second member of the electrode insertion unit acts as a stop to prevent further penetration of the hooks. The hinge for hingedly joining the first and second members is formed of resilient material for maintaining the first and second members in a predetermined position relative to the hinge. This predetermined position has the first and second members at a slight angle with respect to one another with the first member inclined slightly in the direction of the barbless hooks. As the second member is pushed against the heart to insert the hooks and to lie flat on the surface, the first member is bent slightly with respect to the hinge. The resilient force provided by the hinge provides a slight tension on the hooks of the electrode insertion unit and tends to hold the hooks securely in the heart.

BRIEF DESCRIPTION OF THE DRAWINGS

In order that the invention may be clearly understood and readily carried into effect, a preferred embodiment of the invention will now be described, by way of example only, with reference to the accompanying drawings wherein.

DESCRIPTION OF A PREFERRED EMBODIMENT

Figure 2:
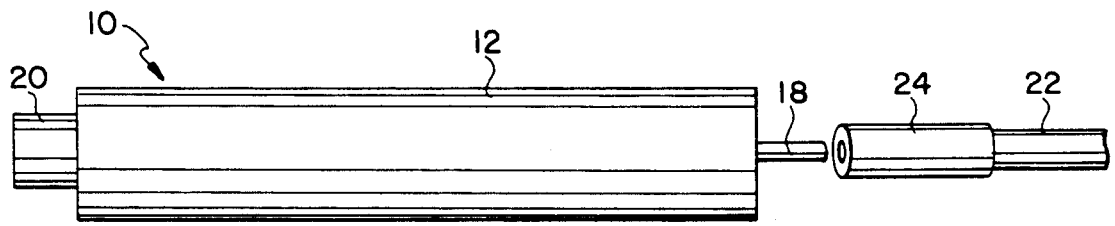
FIG. 2 is an elevational view of the case holding the pulse generating device as shown in FIG. 1 with the conductive lead shown in a detached position.
Figure 1:
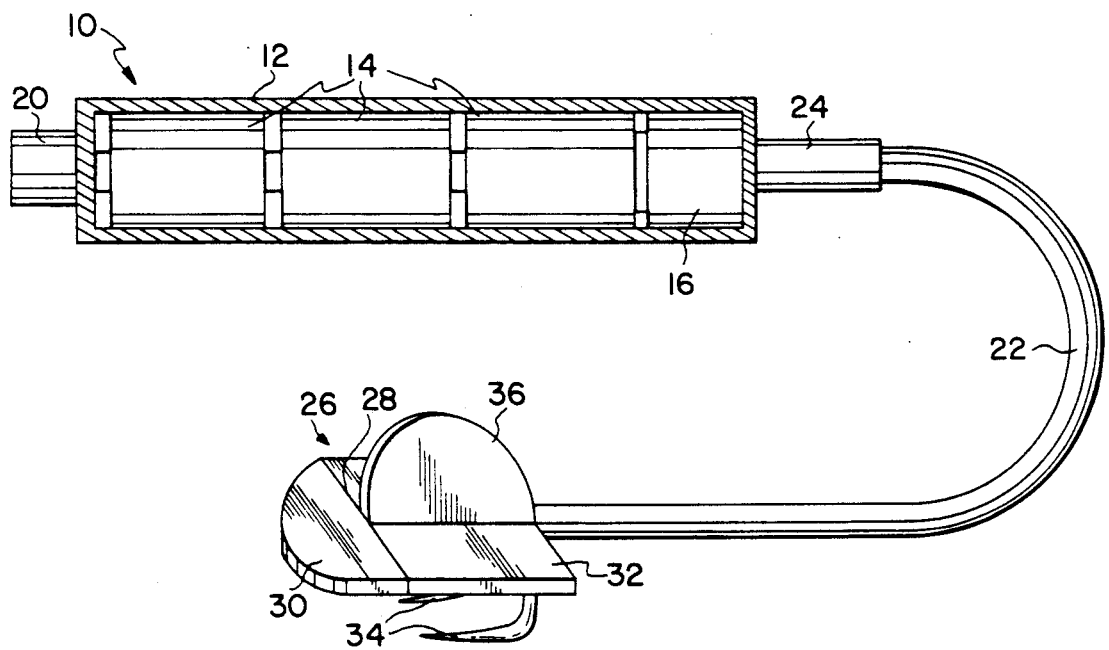
FIG. 1 is a perspective view of a temporary pacemaker according to the present invention with parts broken away.

A preferred embodiment of the present invention is shown in FIG. 1. A temporary pacemaker 10 includes a case 12 for holding batteries 14. The batteries 14 are connected to a repetitive pulse generating circuit 16 which in a preferred embodiment is a single chamber temporary pulse generator Model 5375 circuit manufactured by Nedtronics, Inc. Circuit 16 provides pulses of approximately 20 micro amperes at 60-120 pulses per minute.

The electrical output of circuit 16 is directed to a male output terminal 18 extending outwardly from case 12. A manually operable rheostat 20 is provided on case 12 and is connected to circuit 16. This rheostat 20 includes an "onoff" switch and is used to selectively connect batteries 14 to circuit 16. Further, the rheostat 20 includes a device for manually adjusting the resistance between the electrical circuit 16 and batteries 14 and to select a repetition rate of the pulse train provided by circuit 16.

A disposable conductive lead 22 is provided for connecting pulse generating circuit 16 to an electrode insertion unit 26. The lead 22 includes a female connector 24 attached at one end which connector is shaped to electrically receive the male output terminal 18 provided on case 12.

The electrode insertion unit 26 is connected to a second end of conductive lead 22. The electrode insertion unit 26 in a preferred embodiment is formed from a silicone material by partially cutting through a flat piece of the material along a line to form a hinge 28 between a first member 30 and a second member 32 as shown in FIG. 1. This hinge resiliently maintains the first member 30 and second member 32 in a predetermined position, as will subsequently be described, with respect to hinge 28. A pair of barbless hooks 34 are provided on the underside of second member 32 and protrude outwardly in parallel relation as shown in FIG. 1. Barbless hooks 34 are electrically connected to conductive lead 22.

A gripping tab 36 is provided on the upper side of second member 32. This tab 36 extends upwardly so that a surgeon can easily grasp gripping tab 36 as he manipulates electrode insertion unit 26 to insert barbless hooks 34 into the heart.

As will be noted, when barbless hooks 34 are pushed into the heart, the underside of second member 32 acts as a stop to limit the depth of penetration of hooks 34. The resilient hinge 28 is used to resiliently maintain member 30 in a slightly inclined position relative to second member 32 and extending downwardly toward hooks 34 as shown in FIG. 1. As hooks 34 are inserted in the heart and second member 32 flattened out against the heart surface, the first member 30 springingly acts to provide a slight tension between the electrode insertion unit 26 and the heart surface to hold barbless hooks 34 securely in place.

To use this pacemaker device, the conductive lead 22 with attached electrode insertion unit 26 is removed from a sealed package. The female connector 24 is then connected to male terminal 18 provided on pacemaker case 12. Then with tab 36 of the electrical insertion unit 26, a surgeon manipulates the barbless hooks 34 to pierce the heart tissue and insert the barbless hooks 34 in the heart muscle. Once this has been completed, the surgeon then turns the pacemaker "on" using the on-off control switch of rheostat 20. By manually adjusting the rheostat 20, a pulse repetition frequency for pacing the heart is selected. When the pacemaker 10 has been turned "on", circuit 16 then supplies pulses at the selected rate to male terminal 18 which through conductive lead 22 is connected to the barbless hooks 34. If the pulse rate needs to be changed, rheostat 20 is manually adjusted to obtain the desired pulse repetition frequency. Once the heart has been started, the surgeon can simply pull on lead 22 to remove barbless hooks 34 from the heart, disconnect female connector 24 from male terminal 18 and throw away lead 22 and electrode insertion unit 26. When it is desired to start the heart of a new patient, a new lead 22 and an electrode insertion unit 26 can be removed from another sealed package and the process repeated.

Thus, it can be seen that a disposable, temporary cardiac pacemaker is provided according to the present invention. Lead 22 and electrode insertion unit 26 are disposable. The pacemaker case encloses the batteries, all the electronic circuitry and adjustment controls, and is compactly designed so that it can be placed on or by a patient during surgery. Lead 22, connected to male terminal 18 mounted on case 12, is short, thus decreasing the probability that the lead will be knocked loose during surgery. When lead 22 is removed, male terminal 18 can easily be cleaned for reuse. Further, since batteries are used, the possibility of a detrimental electrical shock is virtually eliminated.

While the fundamental novel features of the invention have been shown and described, it should be understood that various substitutions, modifications and variations may be made by those skilled in the art without departing from the spirit or scope of the invention. Accordingly, all such modifications or variations are included in the scope of the invention as defined by the following claims:

I claim:

1. A disposable pacemaker apparatus for transmitting electrical pulses to a heart, the pacemaker apparatus comprising:
    a battery source for providing electrical power;
    an electrical pulse transmitting means, connected to and powered by the battery, for transmitting a train of electrical pulses;
    a selection means for selecting a pulse rate for the train of pulses within the range of approximately 60 to 120 pulses per minute;
    an electrode insertion unit including:
        a first member;
        a second member having a bottom side and a top side;
        a hinge means for hingedly connecting the first member to the second member;
        resilient means for resiliently maintaining the first and second members in a predetermined position with respect to the hinge means;
        a pair of barbless hooks attached to the bottom side of the second member and protruding in the same direction therefrom said first member attached to the second member for attaching the second member to the heart by pressing the hooks against the heart and drawing the hooks into and far across the heart;
        a gripping tab extending outwardly from the top side of the second member for manipulating the hooks; and an electrically conductive lead having a first end and a second end, the first end being electrically connected to the pulse transmitting means and the second end being connected to the barbless hooks of the electrode insertion unit.

2. A pacemaker apparatus according to claim 1 further including switch means for selectively connecting the battery to the electrical pulse transmitting means.

3. A pacemaker apparatus according to claim 1 further including:

a case for housing the battery source and the pulse transmitting means;
a male output terminal connector positioned on the case and being electrically connected to the pulse transmitting means;
a female connector electrically connected to the electrically conductive lead at the first end thereof;
the female connector being shaped to removably receive the male output terminal connector.

* * * * *